US00PP37589P2

(12) United States Plant Patent
Byrne et al.

(10) Patent No.: US PP37,589 P2
(45) Date of Patent: Aug. 18, 2026

(54) PEACH TREE NAMED 'TRH3B53L'

(50) Latin Name: *Prunus persica*
Varietal Denomination: TRH3B53L

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,164

(22) Filed: Sep. 22, 2025

(51) Int. Cl.
*A01H 5/08* (2018.01)

(52) U.S. Cl.
USPC ..... Plt./194

(58) Field of Classification Search
USPC ..... Plt./194
CPC ..... A01H 6/7463; A01H 5/08
See application file for complete search history.

(56) References Cited

PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.

*Primary Examiner* — Keith O. Robinson
(74) *Attorney, Agent, or Firm* — Dentons US LLP

(57) ABSTRACT

Disclosed is a new variety of *Prunus persica* named 'TRH3B53L'. This new variety, which requires approximately 450 chilling units of dormancy, is considered to be a peach tree of very early season maturity, which produces yellow-fleshed, subacid fruit that are firm, with 50-90% orange-red blush over a yellowish-green ground color, and suitable for fresh market use.

5 Drawing Sheets

Latin name of the genus and species of the plant claimed: *Prunus persica.*

Variety denomination: 'TRH3B53L'.

BACKGROUND OF THE INVENTION

This invention relates to peach trees and, more specifically, to peach trees referred to as a variety of *Prunus persica* named 'TRH3B53L', which requires approximately 450 chilling units of dormancy, produces firm, clingstone, subacid, yellow-flesh peach with 50-90% orange-red blush over a yellowish-green ground color that matures very early in the season. The present peach tree was the result of an ongoing Stone Fruit Breeding Program at College Station, Brazos County, Texas. To this end, controlled crosses were made each year to produce seedling populations from which improved progenies are evaluated and selected. The seedling 'TRH3B53L' was derived from a cross between a low-chill, yellow-flesh, acid, peach selection 'TXW1291-1' (not patented) and a high chill, subacid, yellow-fleshed nectarine, 'Y426-371' (not patented). 'TXW1291-1' was a low-chill, selection made from a large open pollinated population of seedlings with 'Tropic Beauty' (Rouse, R.E. and W.B. Sherman. 1989. 'TropicBeauty': A low-chilling peach for subtropical climates. HortSci. 24(1):165-166, not patented) as a female parent. 'Y426-371' is a high-sugar, subacid nectarine from the Stone Fruit Breeding Program in Parlier, CA. This selection has a complex parentage that includes 'O'Henry' (patented, U.S. Plant Pat. No. 2,964), 'Fairtime' (not patented), 'Southland' (not patented) and 'Sunfre' (not patented; Okie, W.R. 1998. Handbook of peach and nectarine varieties. Agr. Handbook No. 714.). The seed from the cross between 'TXW1291-1' and 'Y426-371' were planted in 2009 in an experimental plot in Floresville, TX. 'TRH3B53L' was marked for subsequent observation in 2011 and noted as having exceptional characteristics.

'TRH3B53L' was bud grafted onto virus-free Nemaguard (not patented, "The Brooks and Olmo Register of Fruit and Nut Varieties," 3rd Ed., American Society of Horticultural Science Press, Alexandria, VA, 1997) peach at the nursery site in Oakdale, CA. The variety was subsequently planted and evaluated as two-year and older trees in Pleasanton (2018-2023), Somerville (2016-2023) and Fairfield (2013-2018), Texas. This evaluation clearly demonstrated that the re-propagated trees were true to the characteristics of the original seedling in all observable aspects.

SUMMARY OF THE INVENTION

The 'TRH3B53L' peach is noteworthy by producing subacid, yellow-fleshed fruit that ripens in the very early season; is firm and has a 50-90% orange-red blush over a yellowish-green ground color. In this regard, the present variety of peach tree bears subacid, yellow-fleshed peaches that are ripe for commercial harvesting and shipment in early to mid-May, when the fruit is grown in the medium chill zone of Texas. 'TRH3B53L' blooms 7-10 days after its female parent TXW1291-1 (not patented) and ~ 10 days before its pollen parent Y426-371 (not patented). It ripens ~2 weeks before its parents. 'TRH3B53L' differs from its yellow-fleshed, acid, peach female parent as it has subacid flesh and differs from its yellow-fleshed, subacid nectarine pollen parent as it is a yellow-flesh peach. This new subacid, yellow-fleshed peach exhibits potential to be commercialized in regions that have chilling accumulation that are relatively low. 'TRH3B53L' as compared to the medium chill, yellow-fleshed peach 'Texking' (U.S. Plant Pat. No. 14,627, 23 Mar. 2004; Byrne, D. H. and T. A. Bacon. 2004. TexKing, an early ripening medium chill peach. HortScience 39:442-443) has reniform versus globose glands, has a low acid versus a traditional acid flavor, and ripens ~5 days earlier than 'Texking'. 'TRH3B53L' as compared to the low chill, yellow-fleshed peach 'TexFirst' (U.S. Plant Pat. No. 26, 199, 24 Nov. 2015; Byrne, D. H. and N. Anderson. 2012. 'TexFirst', An early ripening low chill peach for the subtropics. HortScience 47:1803-1804) has a low acid versus a traditional acid flavor, requires 25 more chilling units to break dormancy for regular cropping, blooms about 2 weeks later than, and ripens about 2 weeks later than 'TexFirst'. 'TRH3B53L' as compared to the selection 'TRH2E68L', a selection with the same pollen parent and a female parent with the same parents, it ripens about one month earlier than 'TRH2E68L'.

BRIEF DESCRIPTION OF THE DRAWINGS

This new variety of peach tree is illustrated by the accompanying photographs of plants in the 5th leaf grown in Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
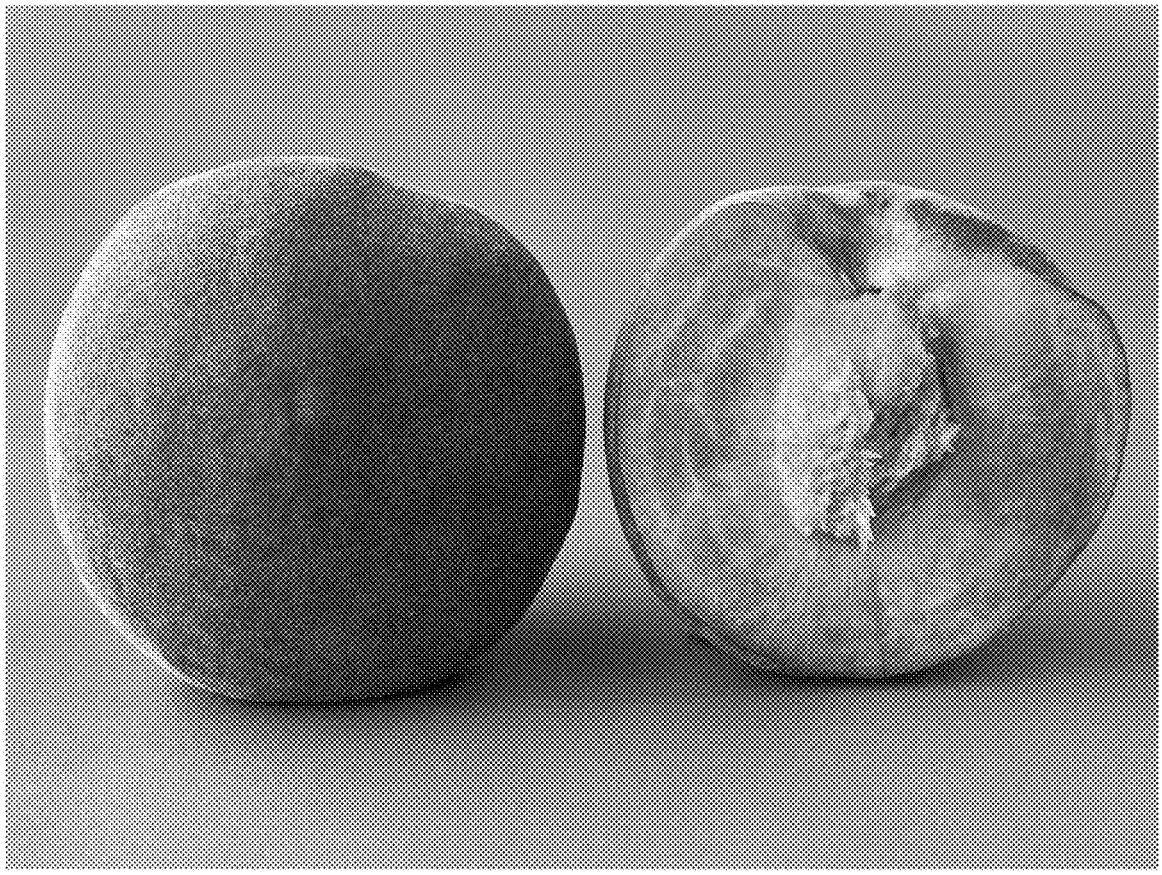
FIG. 1 Fruit of 'TRH3B53L' produced in Pleasanton, Texas showing internal and external coloration.
Figure 2:
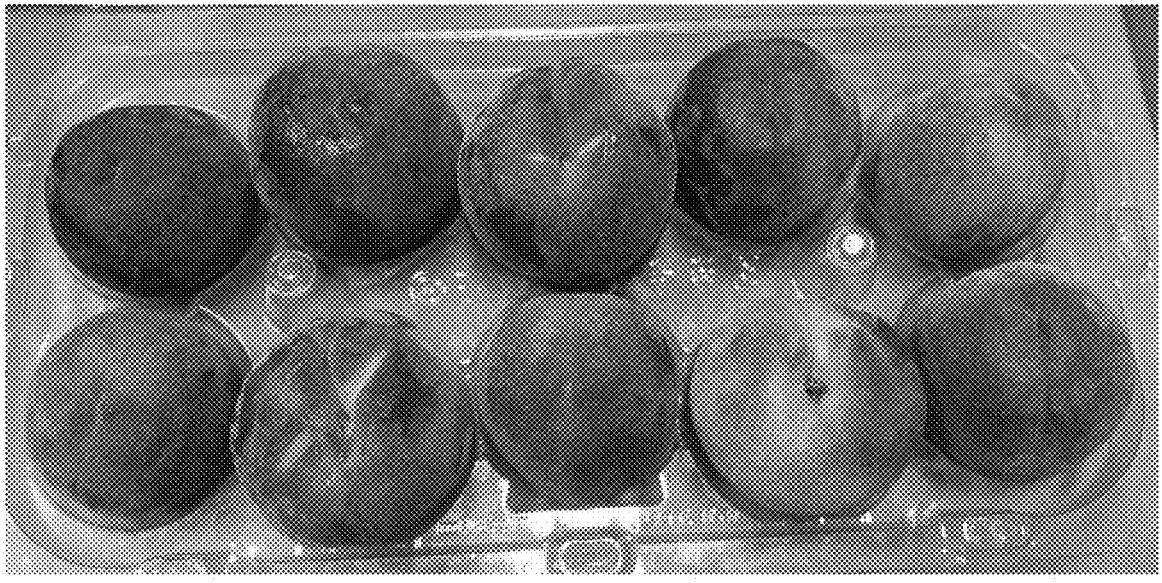
FIG. 2 'TRH3B53L' fruit produced in Pleasanton, Texas showing shape and external coloration.
Figure 3:
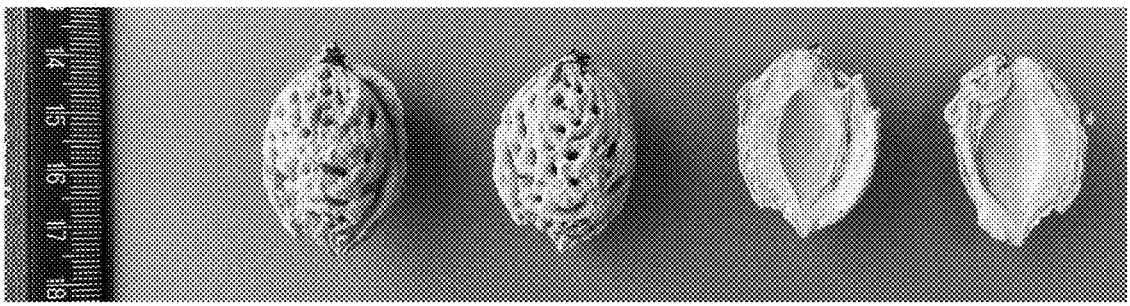
FIG. 3 Photograph of the endocarps of the 'TRH3B53L' peach. The ruler is in centimeters.
Figure 4:
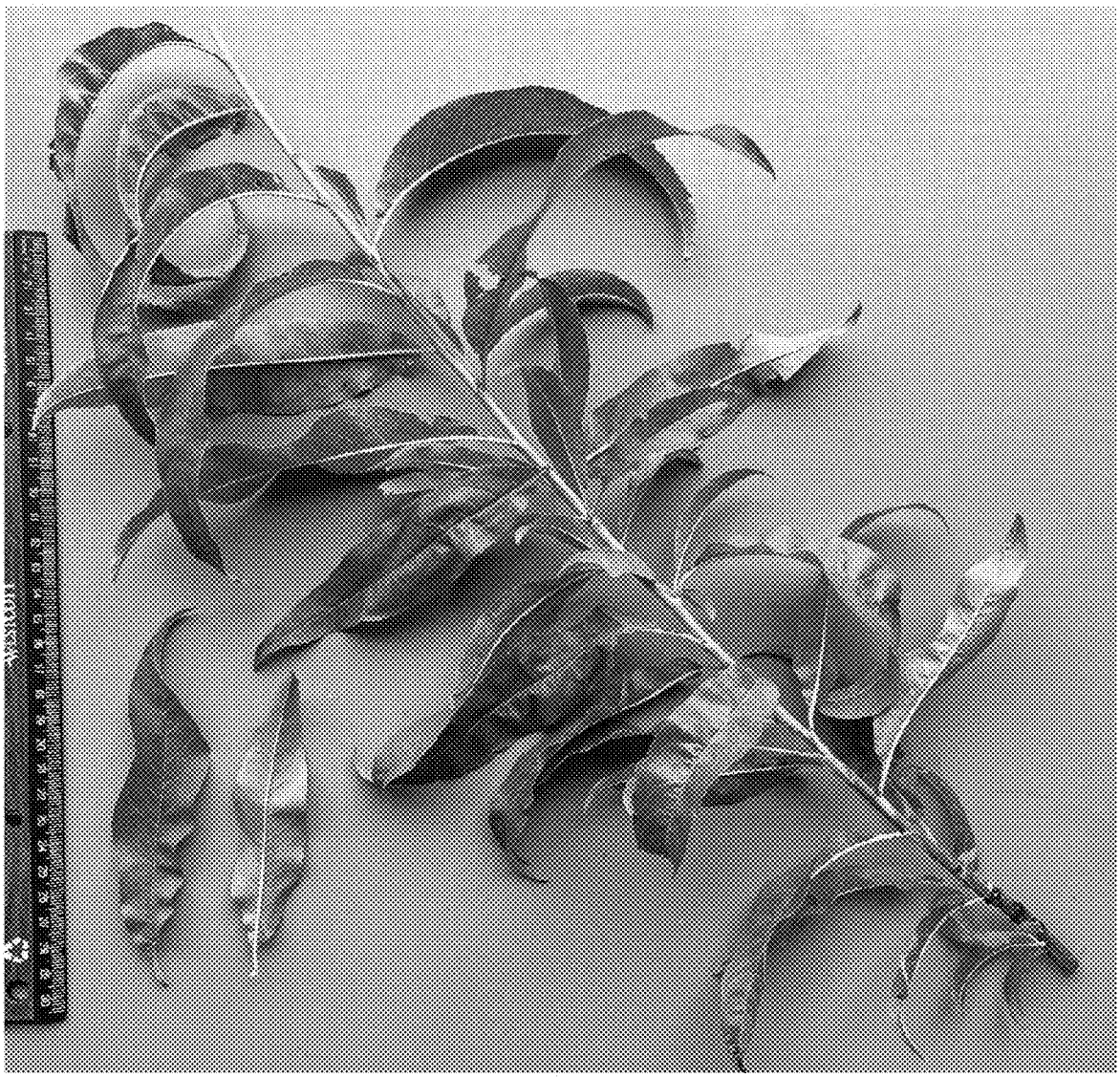
FIG. 4 A stem showing the leaves of the 'TRH3B53L' peach. The ruler is in centimeters.
Figure 5:
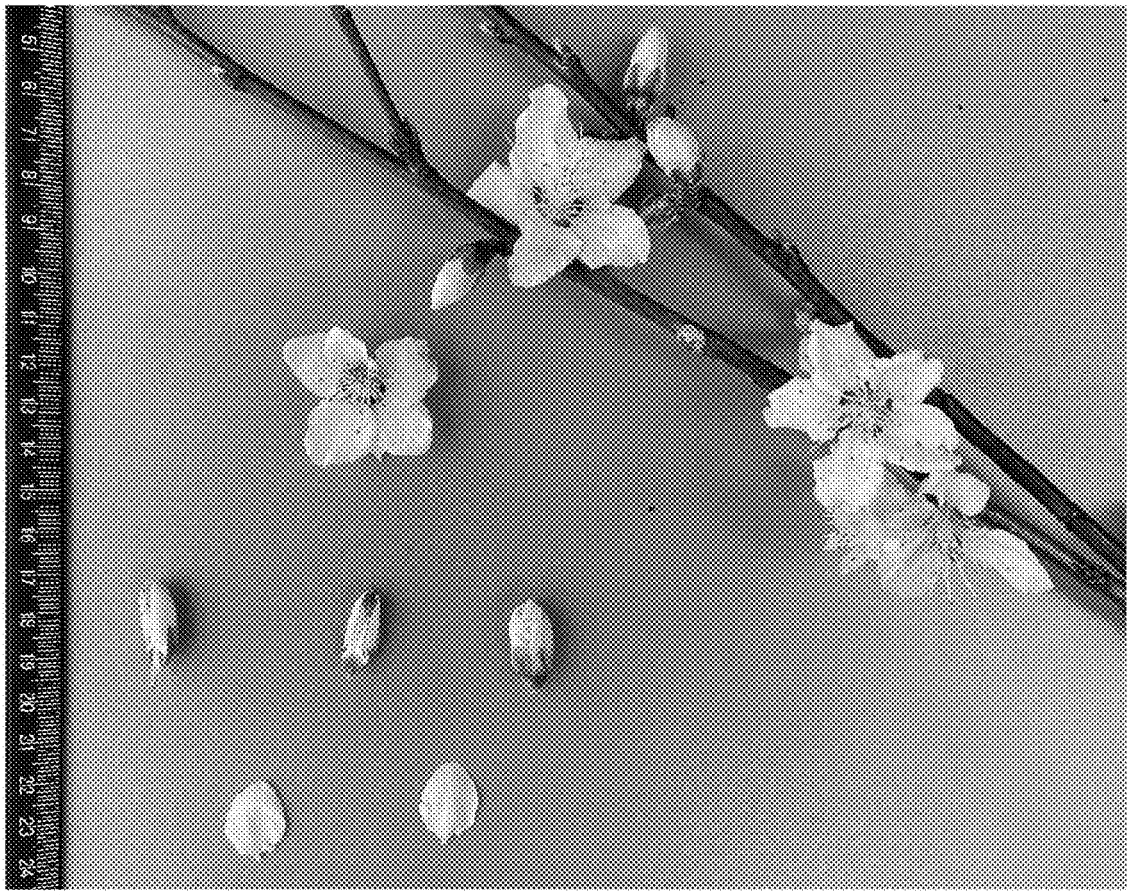
FIG. 5 A stem showing the flowers of the 'TRH3B53L' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars ripening in the early season of maturity.

*Height*.—7 feet (2.1 m) at the end of the 2024 growing season.

*Width*.—6 feet width (1.8 m) at the end of the 2024 growing season.

*Productivity*.—Produces annually in the medium chill zone of Texas without alternate bearing if temperatures of 28° F. or lower are not experienced during bloom. Trees are self-fertile and commonly must be fruit thinned to avoid limb breakage and obtain optimal fruit size. The recommended fruit spacing for early to mid-season ripening fruit cultivars to yield a full crop is one fruit every 6-8" of one-year old fruiting wood. Trees normally set more fruit than needed for a full crop load.

*Shape*.—The 'TRH3B53L' peach has been trained an open center configuration but exhibits a semi spreading growth type as seen in peach varieties 'Texprince' (U.S. Plant Pat. No. 14,629, 23 Mar. 2004; Byrne, D. H. and T. A. Bacon. 2004. TexPrince, a mid-season medium chill peach. HortScience 39 (3): 631-632) and 'Texking' (U.S. Plant Pat. No. 14,627, 23 Mar. 2004; Byrne, D. H. and T. A. Bacon. 2004. TexKing, an early ripening medium chill peach. HortScience 39:442-443).

*Current season growth*.—The current season growth for the new variety was approximately 1.5 to 3 feet (0.46-0.91 m). Average vigor compared to other commercial cultivars grown in the medium chill zone of Texas. Regularity of Bearing — Regular in the absence of temperatures below 28° F. during bloom and considered hardy in the medium chill zone of Texas.

Trunk:

*Size*.—Approximately 2.5 inches (6.4 cm) in diameter and 8.75 inches (22.2 cm) in circumference when measured at approximately 12 inches (30.5 cm) above the soil level, at the end of the 2024 growing season on a three-year old tree.

*Bark texture*.—Considered moderately rough with numerous folds of papery scarf-like skin being present. Bark Coloration — Variable, colors (RHS2001) present are 156C, 156D of the Greyed-White Group, 157A, 157B, 157C of the Green-White Group and 166A and 172A of the Greyed-Orange Group.

Branches:

*Thickness*.—Average to large (about 4 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 5 to 10 mm in width and were approximately 1.5 to 3 mm in height. The lenticel density is 0.8 lenticels per square centimeter.

*Current season shoots*.—Surface texture-Substantially glabrous.

*Internode length*.—Approximately 1.2 to 2.3 cm as measured in the middle of a current season stem. Color of Mature Branches — The predominant colors (RHS2001) are 156A, 156B, 156C, 156D of the Greyed-White Group, 166A and 175A, 175B, 176A, 176B and 176C of the Greyed-Orange Group.

Leaves:

*Size*.—Considered moderately large for the species. Leaf measurements have been taken from vigorous upright current season growth approximately at mid-shoot.

*Leaf length*.—Approximately 159 to 170 mm.

*Leaf width*.—Approximately 35 to 37 mm.

*Leaf thickness*.—Less than 1 mm.

*Leaf form*.—Lanceolate.

*Leaf tip* Form.—Acuminate.

*Leaf upper surface color* (*RHS*2001).—Green varying among 146A and 146B of the Yellow-Green Group.

*Leaf lower surface color* (*RHS*2001).—Green varying among 146B, 146C and 146D of the Yellow-Green Group.

*Leaf lower surface mid-vein color* (*RHS*2001).—Light yellow green (145C, 145D and 150D of the Yellow-Green Group).

*Leaf margins*.—Form — Considered crenate. Uniformity — Considered generally uniform.

*Leaf petioles*.—Length — Approximately 9 to 14 mm. Thickness — Approximately 1 to 1.5 mm. Color (RHS2001) — Pale green (145C, 145D and 150D of the Yellow-Green Group).

*Leaf glands*.—Size — Approximately 1 to 1.5 mm in height and 1 mm in width. Number — Generally 2-4 per leaf. Type — Reniform. Color (RHS2001) — Brown, 165A and 166A of the Greyed-Orange Group and 200B, 200C and 200D of the Brown Group.

*Leaf stipules*.—Length — Approximately 12 to 14 mm. Form — Lanceolate. Color (RHS2001) — Green (144A, 146B and 146C of the Yellow-Green Group) with reddish brown (172A, 175A and 175B of the Greyed-Orange Group) when young. Color is similar on both surfaces. The stipules are considered early deciduous. Ratio of flower buds to vegetative buds — Generally 2 flower buds per vegetative bud.

Flowers:

*Floral buds*.—General — The mature floral buds are conic in form, and slightly appressed relative to the bearing shoot. Color (RHS2001) — The mature buds are medium to dark brown, (approximately 165, 166A, 166B, 172A and 175A of the Greyed-Orange Group, 183A, 183B of the Greyed-Purple Group and 200B, 200C of the Brown Group). Mature Bud Length — Approximately 9 mm. Mature Bud Width — Approximately 4 mm to 5 mm.

*Blooming type*.—Mean date of full bloom in the medium chill zone of Texas was in mid-February (February 18$^{th}$ at Somerville and February 13$^{th}$ at Fairfield experimental plot), a few days before or with the commercial cultivars 'Texking' and 'Flordaking' (not patented, Andrews, 1979. 'Flordaking' peach. HortScience 14(1):81-82.).

*Flower type*.—Showy.

*Flower size*.—Flower diameter at full bloom is approximately 38 to 45 mm.

*Bloom quantity*.—Considered abundant.

*Flower bud frequency*.—Generally 2 per node.

*Petal size*.—Width — Approximately 14 to 15 mm. Length — Approximately 19 to 22 mm.

*Petal form*.—Broadly ovate.

*Petal count*.—Nearly always 5.

*Petal abaxial/adaxial color* (*RHS*2001).—Medium pink when young (65A, 65B, 69A and 73D of the Red-Purple Group and 75D of the Purple Group), becoming darker near the petal claw.

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally — The petal apices appear slightly rounded.

*Flower pedicel*.—Length — Approximately 2 mm. Thickness — Approximately 1 mm. Color (RHS2001) — A light green (N144A, 145A and 145B of the Yellow-Green Group).

*Floral nectaries*.—Color (RHS2001) — Medium orange (24A, 24B, 25A, 25B, 25C, N25B, N25B, N25C, 26A, 28A and 28B of the Orange Group and N163B of the Greyed-Orange Group).

*Sepals*.—Normally 5. Surface Texture — The surface has a short, fine, wooly texture. Size — Width 5 mm, Height 8-9 mm. Sepal form — Ovate. Color (RHS2001) Abaxial or Lower Surface — Maroon with green and grey (approximately 59A, 59B, 60A, 60B and 61A of the Red-Purple Group, 144D, N144D, 145A and 145B of the Yellow-Green Group, 156A, 156B, 156C, 156D of the Greyed-White Group, 157A, 157B, 157C, 157D of the Green-White Group, 178A of the Greyed-Red Group, 183A, 183B, 183C, 184A, 185A, 187B and 187C of the Greyed-Purple Group, 196A, 196B, 196C, 196D, 198C and 198CD of the Greyed-Green Group).

*Floral cup* (*hypanthium*).—Surface Texture — Generally glabrous. Color (RHS2001) — Maroon with green (approximately 59A, 59B, 60A, 60B and 61A of the Red-Purple Group, 144D, N144D, 145A and 145B of the Yellow-Green Group 178A of the Greyed-Red Group and 183A, 183B, 183C, 184A, 185A, 187B and 187C of the Greyed-Purple Group).

*Anthers*.—Color (RHS2001) — Medium yellow with red (approximately 13A, 13B, 13C of the Yellow Group, 14A, 14B, 15A, 15B, 15C, 15D, 16A, 61B, 16C, 17A, 17B, 17C, 17D and 18A of the Yellow-Orange Group, 34A, 34B of the Orange-Red Group, 39A, 47A, 47B and 53B of the Red Group).

*Pollen production*.—Pollen is abundant and is a medium yellow color (RHS2001) (approximately 1A, 11A, 12A, 12B and 12C of the Yellow Group).

*Filaments*.—Size — Variable in length, approximately 15 to 20 mm, with the filaments being equal to the pistil and generally shorter than the petals. Color — White (approximately 155A, 155B, 155C, 155D of the White Group) and darkening with advanced maturity.

*Pistil*.—General — Equal to slightly longer than the anther height and generally shorter than the petals. Length — Approximately 18 to 22 mm, including the ovary. Color (RHS2001) — Considered a very light yellow-green when young (approximately 1C, 1D of the White Group, 2D, 4D and 8C of the Yellow Group, 155A, 155B, 155C of the White Group and 157A, 157B, 157C, 157D of the Green-White Group) and becoming slightly darker with advancing senescence.

*Surface texture*.—The variety has a pubescent style and ovary.

Fruit:

*Maturity when described*.—The present variety of fruit is described, as it would be found in its firm ripe condition at full commercial maturity. Under the ecological conditions prevailing in the medium chill zone of Texas it would be ripe in early to mid May. The average ripe date at Somerville is May 10$^{th}$ and in Fairfield is May 18$^{th}$.

*Size*.—General — Medium large to large for the season and considered uniform. Average Cheek Diameter — Approximately 66 to 73 mm. Average Suture Diameter — Approximately 65 to 72 mm. Average Axial Diameter — Approximately 54 to 68 mm.

*Fruit form*.—Generally considered round. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Medium-dark reddish orange, N34A of the Orange-Red Group and 45A, 46A and 46B of the Red Group.

*Ventral surface*.—Form — Considered uniform.

*Stem cavity*.—Width — Approximately 12 to 22 mm. Length — Approximately 22 to 28 mm. Depth — Approximately 12 to 16 mm.

*Fruit base*.—Round and flat.

*Fruit apex*.—Flat.

*Fruit stem*.—Length — 7 to 8 mm. Thickness — Approximately 4 mm. Color (RHS2001) — Medium brown, 165A, 166A, 166B, 174A, 175A and 175B of the Greyed-Orange Group and N199B of the Grey-Brown Group.

*Fruit skin*.—Generally considered medium or average in thickness. Surface Texture — Light, medium pubescence. Skin Acidity — Considered neutral. Tenacious to Flesh — Yes at commercial maturity. Tendency to Crack — No fruit cracking observed. Skin Color — Generally — Variable, with medium to large amount (approximately 50-90%) of the fruit surface covered with an orange red blush.

*Blush color* (*RHS*2001).—Medium to dark orangish-red, N34A of the Orange-Red Group, 46A, 46B and 53A of the Red Group, 60A of the Red-Purple Group, 178A, 178B of the Greyed-Red Group and 183A, 183B, 185A and 187B of the Greyed-Purple Group.

*Skin ground color*.—(RHS2001) Medium yellowish-green, 1A, 1B, 1C of the Green-Yellow Group and 2B, 3B, 3C, 4A, 5A, 5B and 5C of the Yellow Group.

*Flesh color* (*RHS*2001).—Yellowish-green with maroon, 1A, 1B, 1C of the Green-Yellow Group, 2B, 3B, 3C, 4A, 5A, 5B and 5C of the Yellow Group, 42B, 46B and 47A of the Red Group and 58A, 60D, 61B and 63A of the Red-Purple Group.

*Flesh fibers*.—These fibers are present throughout the flesh.

*Stone cavity color* (*RHS*2001).—Yellowish-green, 1A, 1B, 1C of the Green-Yellow Group and 2B, 3B, 3C, 4A, 5A, 5B and 5C of the Yellow Group.

*Flesh texture*.—Generally, the flesh is considered firm and fine at commercial maturity.

*Ripening*.—Generally the fruit of the present variety ripens evenly.

*Flavor*.—Considered sweet (11.6 Brix) with a rich, subacid flavor.

Stone:

*Attachment*.—Clingstone at commercial maturity.

*Stone size*.—Small to medium size as compared to other commercial peach cultivars. Length — Approximately 29 to 33 mm. Width — Approximately 20 to 25 mm. Thickness — Approximately 16 to 19 mm.

*Fibers*.—Generally a few fibers are attached along the entire surface of the stone.

*Stone form*.—Elliptical.

*Stone base angle*.—Narrow to medium.

*Stone apex angle*.—Medium to wide.

*Stone shape*.—Considered variable. The stone normally ovoid to elongated.

*Stone surface*.—Surface Texture — Consists of single pits, rosettes of pits and chains of pits. Ridges — Numerous fine ridges are present basally and converge towards the base of the stone.

*Ventral edge*.—Medium.

*Dorsal edge*.—Shape — Grooved and having moderately rough edges.

*Stone color* (*RHS*2001).—The color of the dry stone is tan (159A, 159B of the Orange-White Group and 165D of the Greyed-Orange Group). The color of the inside surface of the endocarp is primarily tan, 158A of the Orange-White Group, 159A, 159B, 159C of the Orange-White Group and 164D of the Greyed-Orange Group.

*Tendency to split*.—Splitting is relatively uncommon.

*Kernel*.—The kernel fills the endocarp at harvest and measures approximately 4 mm in thickness, 9-10 mm in width, and 15-18 mm in length. The colors (RHS2001) of the fresh kernel are tan with dark brown lines, 158A, 158B, 158C, 158D of the Yellow-White Group and 164A, 164D, 165A, 177A and 177B of the Greyed-Orange Group. When dried the shriveled kernels measure approximately 1-2 mm in thickness, 7-9 mm in width, and 14-15 mm in length. The colors of the shriveled kernels are primarily medium brown, 164A, 165B and N167A of the Greyed-Orange Group.

*Use*.—The subject variety, 'TRH3B53L', is considered to be a peach tree of early-season maturity, which produces fruit which are firm, yellow-fleshed, subacid, with 50-90% orange-red blush over a yellowish-green ground color, and which are useful for the fresh fruit market.

*Keeping quality*.—Retains firmness and flavor after 14 days of refrigeration at 3-5° C.

*Resistance to insects and disease*.—Moderately susceptible to bacterial leaf spot (*Xanthamonas campestris* cv. pruni) similar to that seen in the cultivar 'TexKing'. Otherwise, no atypical resistances or susceptibilities have been noted under normal cultural conditions to date.

*Shipping quality*.—Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH3B53L', as illustrated and described herein.

* * * * *